United States Patent
Fontana et al.

(10) Patent No.: US 7,321,062 B2
(45) Date of Patent: *Jan. 22, 2008

(54) PROCESS FOR THE PREPARATION OF (PER) FLUORINATED MONO-FUNCTIONAL CARBONYL COMPOUNDS

(75) Inventors: Giovanni Fontana, Verona (IT); Walter Navarrini, Milan (IT)

(73) Assignee: Solvay Solexis S.p.A., Milan (IT)

( * ) Notice: Subject to any disclaimer, the term of this patent is extended or adjusted under 35 U.S.C. 154(b) by 609 days.

This patent is subject to a terminal disclaimer.

(21) Appl. No.: 10/753,548

(22) Filed: Jan. 9, 2004

(65) Prior Publication Data

US 2004/0147780 A1  Jul. 29, 2004

(30) Foreign Application Priority Data

Jan. 9, 2003  (IT) ............... MI2003A0018

(51) Int. Cl.
  C07C 45/00  (2006.01)
  C07C 53/38  (2006.01)
  C07C 51/58  (2006.01)
(52) U.S. Cl. ............. 562/864; 562/849; 568/407
(58) Field of Classification Search .......... 562/840, 562/849, 852, 856, 861, 862; 568/418
  See application file for complete search history.

(56) References Cited

U.S. PATENT DOCUMENTS

| | | | |
|---|---|---|---|
| 3,113,967 A | 12/1963 | Fawcett | |
| 3,175,378 A | 3/1965 | Russell | |
| 3,250,808 A | 5/1966 | Moore, Jr. et al. | |
| 3,847,978 A | 11/1974 | Sianesi et al. | |
| 4,499,024 A | 2/1985 | Fifolt | |
| 4,827,024 A | 5/1989 | Guglielmo et al. | |
| 5,149,842 A | 9/1992 | Sianesi et al. | |
| 5,258,110 A | 11/1993 | Sianesi et al. | |
| 5,488,142 A | 1/1996 | Fall et al. | |
| 5,488,181 A | 1/1996 | Marchionni et al. | |
| 5,756,841 A * | 5/1998 | Desmarteau et al. | 562/849 |
| 6,013,795 A | 1/2000 | Manzara et al. | |
| 6,127,498 A | 10/2000 | Tonelli et al. | |

FOREIGN PATENT DOCUMENTS

| | | |
|---|---|---|
| EP | 0 754 670 A2 | 1/1997 |
| GB | 1104482 | 4/1965 |
| GB | 1189337 | 7/1967 |

OTHER PUBLICATIONS

"A Simple Synthesis of Fluoroxyperfluoroalkyl Compounds," John K. Ruff et al., Communications to the Editor, Journal of the American Chemical Society, 88:19, Oct. 5, 1966, pp. 4531-4532.

"Bis(fluoroxy)difluoromethane, $CF_2(OF)_2$," Frederick A. Hohorst et al., Journal of the American Chemical Society, 89:8, Apr. 2, 1967, pp. 1809-1810.

"The Catalytic Addition of Fluorine to a Carbonyl Group. Preparation of Fluoroxy Compounds," Max Lustig et al., Journal of the American Chemical Society, 89:12, Jun. 7, 1967, pp. 2841-2843.

"Advances in the Chemistry of Organofluorine Hypohalites and Related Compounds," F. M. Mukhametshin, Russian Chemical Reviews, 49 (7), 1980, pp. 668-682.

* cited by examiner

*Primary Examiner*—Karl Puttlitz
(74) *Attorney, Agent, or Firm*—Arent Fox LLP

(57) ABSTRACT

A process for the synthesis of (per)fluorinated mono-functional carbonyl compounds having the following formula:

$$F-A-(R_F)_t-B-C(O)X_1 \qquad (I)$$

wherein:
$X_1=F, CF_3$;
$t=0, 1$;
A, B equal to or different from each other, are independently $C_1-C_5$ (per)fluoroalkylene groups or $C_1-C_5$ (per)fluorooxyalkylene groups;
$R_F$ is $-Rf_1-$, $C_1-C_{20}$ perfluoroalkylene, $-ORf_1O-$; or $-ORf_2-$, wherein $Rf_2$ is a perfluorooxyalkylene chain;
wherein the carbonyl groups of a (per)fluorinated di-functional carbonyl compound of formula (III):

$$X_2(O)C-A-(R_F)_t-B-C(O)X_1 \qquad (III)$$

wherein:
$X_1$, $R_F$, t, A and B have the above meanings;
$X_2$, equal to or different from $X_1$, has the same meanings as $X_1$; are partially fluorinated with elemental fluorine in the presence of a catalyst having formula MeFy.zHF, Me being an alkaline or alkaline-earth metal or Ag, y=1 or 2, z an integer from 0 to 4,
carrying out said reaction at a temperature higher than a temperature such that it leads to the formation of $C(O)FX_2$.

18 Claims, No Drawings

PROCESS FOR THE PREPARATION OF (PER) FLUORINATED MONO-FUNCTIONAL CARBONYL COMPOUNDS

The present invention relates to a process for preparing (per)fluorinated mono-functional carbonyl compounds in high yields, starting from (per)fluorinated di-functional carbonyl compounds.

Various methods for obtaining (per)fluorinated mono-functional carbonyl compounds are known.

U.S. Pat. No. 3,113,967 describes the synthesis of perfluoromono-acyl-fluorides by condensation of $COF_2$ with perfluoroolefins. In the reaction, as catalysts, salts capable to make available the ion fluoride are used and optionally dipolar aprotic solvents can be used. This process has the drawback to be limited by the need to have available cheap fluoroolefins. Besides, the Examples show that high yields are obtained only when one operates in the presence of a solvent.

U.S. Pat. No. 3,250,808 describes perfluoromonoacylfluorides of formula $Rf_1O[CF(CF_3)CF_2O]_{nI}CF(CF_3)C(O)F$ wherein nI=100, and the process for their preparation. The synthesis has the drawback to require the use of the perfluoropropene epoxide (HFPO), which must be previously prepared by controlled perfluoropropene oxidation. A further drawback is that a dipolar aprotic solvent must be used at the anhydrous state.

U.S. Pat. No. 6,013,795 describes a new class of fluoroalkylcarbonyl compounds alpha branched to carbonyl. Said compounds, preferably having at least 8 carbon atoms, are synthesized starting from the corresponding hydrogenated precursors according to the classic fluorination methods with $F_2$, or the electrochemical route with HF. The drawback of this process is that in the fluorination high amounts of fluorine per mole of synthesized perfluoroacylfluoride must be used. Besides, in some cases, for example when oxygen atoms are present in the starting compound, the hydrofluoric acid formed during the fluorination causes the decompostion of the molecule to be fluorinated.

U.S. Pat. No. 3,847,978 describes the preparation of perfluoropolyether acylfluorides of formula $AO(C_3F_6O)_{mIV}(C_2F_4O)_{lIV}(CF_2O)_{nIV}$—B wherein A and B equal or different from each other can be: $-CF_3$, $-C(O)F$, $-CF_2C(O)F$, $-CF(CF_3)C(O)F$, $-CF_2C(O)CF_3$. The process requires the reduction of a peroxidic linear perfluoropolyether polymer of formula: A-O $(C_3F_6O)_{mIV}(C_2F_4O)_{lIV}(CF_2O)_{nIV}(O)_{sIV}$—B, wherein A and B have the above meaning. The Examples show that the process has a high selectivity for obtaining perfluoropolyether diacylfluorides (acylfluoride groups in both end groups A and B), while the selectivity is poor for the monofunctional acylfluoride derivatives.

EP 754,670 describes mono-hypofluorite compounds of formula $FC(O)$—$Rf_{III}$—$CF_2OF$, wherein $Rf_{III}$ is a $C_1$-$C_{12}$ perfluoroalkylene or perfluorooxyalkylene chain having a molecular weight in the range 100-2,000, and the process for the preparation thereof. The process requires the hypofluorite synthesis in liquid phase, in the presence of a catalyst, by fluorination of diacylfluorides at temperatures in the range from $-40°$ C. to $+40°$ C. The used catalysts are the salts of general formula $MeF_{y'}.zHF$, wherein Me is an alkaline or alkaline-earth metal, for example $KHF_2$ or $CsHF_2$. In the patent it is shown that by using an alkaline or alkaline-earth metal fluoride catalyst of formula $MeF_{y'}$, only bis-hypofluorites are obtained. In particular in the comparative Examples it is shown that by using in the reaction CsF or KF, by operating at the temperature of $-10°$ C., a mixture formed of bis-hypofluorites and starting reactants is obtained.

The need was felt to have available a synthesis of (per)fluorinated mono-functional carbonyl compounds to be made in a semicontinuous and continuous way, even in the absence of a solvent, having better yields of mono-functional carbonyl (per)fluorinated compounds.

The Applicant has surprisingly and unexpectedly found a process for preparing monocarbonyl (per)fluorinated compounds solving the above technical problem.

It is an object of the present invention a process for the synthesis of (per)fluorinated mono-functional carbonyl compounds having the following formula:

$$F-A-(R_F)_t-B-C(O)X_1 \quad (I)$$

wherein:

$X_1$=F, $CF_3$;

t=0, 1;

A, B equal to or different from each other, can independently be $C_1$-$C_5$ (per)fluoroalkylene groups or linear or branched $C_1$-$C_5$ (per)fluorooxyalkylene groups, optionally containing one or more Cl and/or H atoms;

$R_F$ is selected from the following groups:
—$Rf_1$—, —$ORf_1O$— wherein $Rf_1$=$C_1$-$C_{20}$ perfluoroalkylene; —$ORf_2$—, wherein $Rf_2$ is a perfluorooxyalkylene chain containing one or more of the following units statistically distributed along the backbone:

($C_3F_6O$), selected between ($CF_2CF(CF_3)O$) or ($CF(CF_3)CF_2O$);

($CFX_1O$) wherein $X_1$ is F or $CF_3$;

($C_2F_4O$);

($CF_2(CF_2)_{x'}$, $CF_2O$) wherein x' is an integer equal to 1 or 2;

($CR_4R_5CF_2CF_2O$) wherein $R_4$ and $R_5$ are equal to or different from each other and selected between H, Cl, and wherein one fluorine atom of the perfluoromethylene unit can be optionally substitued with H, Cl or (per)fluoroalkyl, having for example from 1 to 4 carbon atoms;

wherein the carbonyl groups of a (per)fluorinated di-functional carbonyl compound of formula:

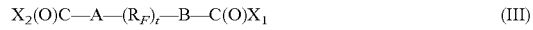

$$X_2(O)C-A-(R_F)_t-B-C(O)X_1 \quad (III)$$

wherein:

$X_1$, $R_F$, t, A and B have the above meanings;

$X_2$, equal to or different from $X_1$, has the same meanings as $X_1$;

are fluorinated with elemental fluorine in the presence of a catalyst based on metal fluorides having formula $MeFy.zHF$, Me being an alkaline or alkaline-earth metal or Ag, y=1 or 2, z an integer from 0 to 4, z preferably being 0 or 1, particularly preferred z=0, carrying out the reaction at a temperature such that it leads to the formation of $C(O)FX_2$ wherein $X_2$ is as above, said fluorination being carried out by using a fluorine amount at most equal to that necessary to obtain the total conversion of the starting compound (III).

It is clear that the fluorination reaction can be carried out also using a fluorine amount higher than that above defined. However working in this way, a yield reduction can take place.

In practice, in the invention process, the (per) fluorinated mono-hypofluorite compound of formula $$FO—CFX_2—A—(R_F)_t—B—C(O)X_1 \quad (II)$$

wherein $X_1$, $X_2$, A, B, $R_f$, t are as above, immediately decomposes since the reaction temperature is at least equal to, preferably higher than the decomposition temperature of the monohypofluorite (II).

The invention process follows the reaction scheme:

$$X_2(O)C—A—(R_F)_t—B—C(O)X_1 \quad (III) + F_2 \xrightarrow{catal.}$$

$$F—A—(R_F)_t—B—C(O)X_1 \quad (I) + C(O)FX_2.$$

Preferably when t=0 and $X_1=X_2=F$, A or B is different from —$CF_2$—.

The preferred A and B groups in the formulas (I)-(III) are selected from the following:

—$CF_2$—, —$CF(CF_3)$—, —$CF_2CF_2$—, —$CF_2CF_2CF_2$—, —$CF_2CF(CF_3)$—, —$CF(CF_3)CF_2$—, —$CF(OCF_3)$—, —$C(OCF_3)_2$—, —$C(CF_3)(OCF_3)$—.

Preferably, when $R_F$=—$ORf_2$—, the perfluorooxyalkylene chain $Rf_2$ is selected from the following:

a') —$(CF_2CF_2O)_m(CF_2O)_n(CF_2CF(CF_3)O)_p(CF(CF_3)O)_q(CF_2CF_2CF_2O)_r$—, b') —$(CF_2O)_n(CF_2CF(CF_3)O)_p(CF(CF_3)O)_q$—, c') —$(CF_2CF_2O)_m(CF_2O)_n$—, wherein:
m is comprised between 0 and 100, extremes included,
n is comprised between 0 and 100, extremes included,
p is comprised between 0 and 60, extremes included,
q is comprised between 0 and 60, extremes included,
r is comprised between 0 and 60, extremes included, m+n+p+q+r being≧0 and the number average molecular weight of —$ORf_2$— in the range 16-12,000, preferably 16-6,000, still more preferably 60-4,000.

In particular in the formula c') m and n, independently the one from the other, have the above values and, preferably, when m and n are both present, are such whereby m/n ranges from 0.2 to 12 with a number average molecular weight of —$ORf_2$— within the above values.

The reaction temperature ranges from 0° C. to +300° C., preferably from +40° C. to +200° C.

The process can be carried out in the presence or in the absence of solvents, inert under the reaction conditions, preferably in the absence of solvents.

When solvents are used, they are selected for example among the following: $C_3F_8$, $C_4F_8$(cycle), $C_3F_8O$(ether), $C_4F_{10}O$(ether), $CF_3O(CF_2)_2$—$CF_3$, $CF_4$, $C_2F_6$, perfluoropolyethers.

The fluorine conversion is generally higher than 80%.

The invention process is carried out in a semicontinuous or in a continuous way in an only reactor.

The gaseous fluorine, optionally diluted with a gas inert under the reaction conditions, for example nitrogen and helium, is fluxed at the above temperatures until obtaining the desired conversion percentage of the initial carbonyl end groups, in the range 5-90%, preferably 10%-80%.

The conversion percentage of the initial carbonyl end groups can for example be determined by $^{19}F$-NMR.

The most preferred metal fluoride catalysts, as said, have in the formula MeFy.zHF z=0, i.e. they do not contain hydrogen atoms in their formula. In particular as preferred catalysts the following catalysts are mentioned:

alkaline or alkaline-earth metal fluorides selected from the following: CsF, KF, RbF, LiF, NaF, $CaF_2$, $BaF_2$, $MgF_2$, $SrF_2$;

AgF;

said catalysts can be used as such, or mixed with each other or optionally supported on porous material.

As porous support material, it can be used the porous materials available on the market and inert under the reaction conditions. $AlF_3$ can for example be mentioned.

The preferred metal fluorides are CsF, KF, NaF, $CAF_2$.

The catalyst can be used for long periods in the process according to the present invention, without the need to be regenerated.

The % weight ratio between the catalyst and the compound of formula (III) is from 0.01% to 15%, preferably from 0.5% to 10%.

The fluorination reaction can be carried out at a pressure equal to or higher than the atmospheric pressure, for example up to 5 atmospheres.

From a practical point of view, to determine the process temperature, one determines first the temperature $T_i$, decomposition temperature of the hypofluorite of formula (II), by heating slowly, for example 1° C./min, a sample of the monohypofluorite (II) and detecting, by IR analysis, the appearance of the peaks corresponding to the species C(O)$FX_2$ ($COF_2$, signals at 1928, 1944, 1956 $cm^{-1}$ and/or $CF_3COF$ signal at 1898 $cm^{-1}$). See the Examples. The process temperature, as said, must be equal to or preferably higher than the decomposition temperature $T_i$ of the hypofluorite of formula (II).

In the semicontinuous process the gaseous fluorine, optionally diluted with a gas inert under the reaction conditions as above indicated, is fed at the reaction temperatures in the suspension containing the catalyst and the di-functional carbonyl compounds (III). The fluorine is fed until obtaining the desired conversion percentage of the starting carbonyl end groups into the above range, forming neutral F—A— end groups (perfluoroalkyl or perfluorooxyalkyl) of formula (I) as above defined.

The yield in neutral perfluoroalkyl or perfluoro-oxyalkyl end groups with respect to the converted carbonyl end groups is higher than 90%, preferably higher than 95%.

At the end of the reaction, the reaction compounds are separated from the catalyst and from the optional solvent by using known separation methods, as, for example, filtration, distillation or stripping under vacuum.

In the continuous process the fluorination reaction can be carried out by separately feeding on the catalyst gaseous fluorine, optionally diluted with an inert gas selected among those above mentioned, and the di-functional carbonyl (per) fluorinated compound (III).

The reaction raw product, containing the unreacted di-functional carbonyl compounds, the mono-functional carbonyl compounds and those having both the end groups neutral, is continuously taken from the reactor bottom and optionally recycled in the same reactor, repeating the invention process until obtaining the desired conversion percentage of the starting carbonyl end groups into neutral F—A— end groups. This percentage is in the range mentioned above for the semicontinuous process.

The final raw reaction product is collected and the products separated and purified, for example by distillation.

The continuous process has the advantage that the final product is easily separated from the catalyst.

With the invention processes one can operate even under such conditions that in the reaction mixture the (per)fluorinated di-functional carbonyl compounds of formula (III) are substantially absent, by using the minimum fluorine amount necessary to obtain the total conversion of the starting compound (III). See the Examples.

The total conversion of the starting compound is determined by GC/MS analysis, until disappearance of the starting compound.

The fluorination reaction can be carried out also using an amount of fluorine higher than that above defined. However working in this way can bring to a yield reduction. The complete conversion of the perfluorinated di-functional carbonyl compounds of formula (III) in the reaction mixture is particularly useful from the industrial point of view since it allows an easy separation of the (per)fluorinated mono-functional carbonyl compounds of formula (I) from the reaction mixture; to separate the compound (I) it is preferable to transform it into its functional derivatives, for example acids, esters, or amides, preferably acids.

The (per)fluorinated di-functional carbonyl compounds of formula (III) can be prepared by synthesis of the peroxidic raw product and subsequent reduction. The peroxidic raw product synthesis is carried out by oxidative polymerization of fluoroolefins, in particular $C_3F_6$ and/or $C_2F_4$, with oxygen at a low temperature in the presence of UV light or of a radical initiator, as described for example in patents GB 1,189,337, GB 1,104,482, U.S. Pat. No. 3,683,027, U.S. Pat. No. 3,175,378, U.S. Pat. No. 5,149,842, U.S. Pat. No. 5,258,110, U.S. Pat. No. 5,488,181.

The reduction of the peroxidic raw product is carried out with hydrogen on a suitable catalyst containing palladium to give di-functional carbonyl perfluoropolyether compounds, for example as described in U.S. Pat. No. 3,847,978, U.S. Pat. No. 6,127,498. Furthermore the di-functional carbonyl compounds are obtainable by direct fluorination, as described for example in U.S. Pat. No. 5,488,142.

The catalysts used in the present invention process are known in the art. U.S. Pat. No. 4,827,024, U.S. Pat. No. 4,499,024, EP 754,670; Ruff J. K. et al., J. Am. Chem Soc. 88:19 (1966), 4531-4532; Lustig et al., J. Am. Chem. Soc. 89:12 (1967), 2841-2843; Hohorst A. et al., J. am Chem Soc. 89:8 (1967), 1809-1810 can be mentioned.

The preferred di-carbonyl (per)fluorinated compounds of formula (III) to carry out the invention process are selected from the following:

$X_2(O)CCFY_2—O(CF_2O)_n(CF_2CF(CF_3)O)_p(CF(CF_3)O)_q—CFY_1C(O)X_1$, $X_2(O)CCFY_2—O(CF_2CF_2O)_m(CF_2O)_n—CFY_1C(O)X_1$, wherein:

$X_1, X_2$, equal or different, are as above, $Y_1, Y_2$, equal or different, have the $X_1$ meaning, m, n, p, q are as above. Still more preferred among the formula (III) compounds are the following:

$F(O)CCF_2O(CF_2O)_n—CF_2C(O)F$, $F(O)CCF_2O(CF_2CF_2O)_m—CF_2C(O)F$, $F(O)CCF_2O(CF_2CF_2O)_m(CF_2O)_n—CF_2C(O)F$, wherein m and n are as above defined. Among the compounds of formula (III) the following ones are further preferred:

$F(O)CCF_2OCF_2C(O)F$, $F(O)CCF_2OCF_2OCF_2C(O)F$, $F(O)CCF_2OCF_2CF_2OCF_2C(O)F$, $F(O)CCF_2OCF_2OCF_2CF_2OCF_2C(O)F$, $F(O)CCF_2OCF_2OCF_2OCF_2C(O)F$, $F(O)CCF_2OCF_2CF_2OCF_2CF_2OCF_2C(O)F$.

The preferred mono-functional carbonyl (per)fluorinated compounds of formula (I) are the following:

$CF_3—O(CF_2O)_n(CF_2CF(CF_3)O)_p(CF(CF_3)O)_q—CF_2C(O)F$, $CF_3CF_2—O(CF_2O)_n(CF_2CF(CF_3)O)_p(CF(CF_3)O)_q—CF(CF_3)C(O)F$, $CF_3CF_2—O(CF_2O)_n(CF_2CF(CF_3)O)_p(CF(CF_3)O)_q—CF_2CF_2C(O)F$, $CF_3—O(CF_2CF_2O)_m(CF_2O)_n—CF_2C(O)F$, $CF_3CF_2—O(CF_2CF_2O)_m(CF_2O)_n—CF(CF_3)C(O)F$, $CF_3CF_2—O(CF_2CF_2O)_m(CF_2O)_n—CF_2CF_2C(O)F$, wherein m, n, p and q are as above. The following formula (I) compounds are still more preferred:

$CF_3OCF_2C(C)F$, $CF_3OCF_2OCF_2C(O)F$, $CF_3OCF_2CF_2OCF_2C(O)F$, $CF_3OCF_2OCF_2CF_2OCF_2C(O)F$, $CF_3OCF_2CF_2OCF_2OCF_2C(O)F$, $CF_3OCF_2OCF_2OCF_2C(O)F$, $CF_3OCF_2CF_2OCF_2CF_2OCF_2C(O)F$.

It has been surprisingly found by the Applicant that it is possible to use the alkaline or alkaline-earth metal fluoride catalysts as above defined to obtain the mono-functional carbonyl (per) fluorinated compounds of formula (I) by fluorination according to the invention process of di-functional carbonyl (per)fluorinated compounds of formula (III). This is quite unexpected since according to the above prior art these catalysts are not useful to obtain (per)fluorinated mono-functional carbonyl compounds (I) from (per) fluorinated di-functional carbonyl compounds (III).

Furthermore it has been surprisingly found by the Applicant that said catalysts can be used for long periods of time, without being regenerated, even operating in the same reactor wherein the hypofluorite decomposition takes place.

The perfluorinated mono-functional carbonyl compounds are important compounds in the chemical industry. The perfluorinated mono-acyl fluorides can be transformed into other functional groups as acids, salts, esters, amides, ethers. Said derivatives are usefully employed as surfactants or additives, or as intermediates for the synthesis of various fluorinated derivatives.

Furthermore mono-acylfluorides are useful compounds for the preparation of perfluorovinylethers by the fluorination to the ccorresponding hypofluorites and subsequent sum to (per)-fluoroolefins, for example CFCl=CFCl. Said monomers are used in the synthesis of fluoroelastomers and fluoroplastomers.

Besides, mono-acyl fluorides are used for the preparation of perfluorodiacyl-peroxides, polymerization initiators useful for obtaining fluoropolymers having perfluorinated end groups.

The following non limitative Examples illustrate the invention.

EXAMPLES

Example 1A

Comparative

Determination of the decomposition temperature $T_i$ of hypofluorites obtained by fluorination of the corresponding diacylfluorides $F(O)CCF_2O\text{---}(CF_2CF_2O)_m(CF_2O)_n\text{---}CF_2C(O)F$ (IIIA) number average MW (MN) 620 on CsF catalyst at the temperature of $-10°$ C.

In a 10 cc metal reactor equipped with internal thermocouple there are introduced 1.0 g of CsF catalyst (Aldrich®, titre 99.9%), which is dried by heating under vacuum at 200° C. for two hours and successively fluorinated at 400 mbar ($4\times10^4$ Pa) of fluorine at the temperature of 150° C. for 2 hours. After elimination of the residual fluorine, 2 mmoles of diacylfluorides are introduced, having formula:

$$F(O)CCF_2O\text{---}(CF_2CF_2O)_m(CF_2O)_n\text{---}CF_2C(O)F \quad \text{(IIIA),}$$

number average MW (MN) 620, m/n ratio=4.30 and functionality in —COF end groups of 1.82 and functionality in —$CF_2CF_3$ end groups of 0.18, determined by NMR. The diacylfluoride has been prepared as described in U.S. Pat. No. 5,258,110 and U.S. Pat. No. 3,847,978.

After cooling in liquid nitrogen ($-196°$ C.), the optional uncondensable products ($N_2$, $O_2$) stripped, 1.82 mmoles of fluorine are added and the reaction mixture is brought to $-10°$ C. and maintained at this temperature for 4 hours. It is cooled to $-196°$ C. and it is noticed that the fluorine conversion is complete. The reaction mixture is then let reach $-10°$ C. without variation of the internal pressure, which indicates that the hypofluorites formed under said conditions are stable. Then the temperature is slowly increased, with a gradient of 1° C./min. under temperature and internal pressure control. At the temperature of about 40° C. it is observed the decomposition of the obtained hypofluorites whith exothermal reaction and $COF_2$ formation, as detected by IR analysis of the gaseous phase.

Example 1B

Comparative

Determination of the decomposition temperature $T_i$ of hypofluorites obtained by fluorination of the corresponding diacylfluorides $F(O)CCF_2O\text{---}(CF_2CF_2O)_m(CF_2O)_n\text{---}CF_2C(O)F$ (IIIB) number average MW (MN) 460 on CsF catalyst at the temperature of $-10°$ C.

The Example 1A is repeated by using the above diacylfluoride. The decomposition temperature results of about 40° C.

Example 1

Syntesis in a semicontinuous way of monoacylfluoride $CF_3O\text{---}(CF_2CF_2O)_m(CF_2O)_n\text{---}CF_2C(O)F$ by performing the fluorination of the corresponding diacylfluorides over CsF catalyst at the temperature of 90° C.

In a 420 cc metal reactor equipped with reflux condenser, mechanical stirrer and internal thermocouple there are introduced 12.5 g of CsF catalyst (Aldrich®, titre 99.9%), which is dried under inert gas stream at the temperature of 200° C. for 4 hours and successively fluorinated with 1 Nl/h of $F_2$ diluted with 1 Nl/h of He at the temperature of 150° C. for 4 hours.

After elimination of the residual fluorine, 100 g (0.161 moles) of diacylfluoride (IIIA) are introduced, having formula:

$$F(O)CCF_2O\text{---}(CF_2CF_2O)_m(CF_2O)_n\text{---}CF_2C(O)F \quad \text{(IIIA),}$$

average number MW (MN) 620, m/n ratio=4.30 and functionality in —COF end groups of 1.82 and functionality in —$CF_2CF_3$ end groups of 0.18, determined by NMR. The diacylfluyoride has been prepared as described in U.S. Pat. No. 5,258,110 and U.S. Pat. No. 3,847,978.

The reaction mixture is brought to 90° C. by a thermostatic oil bath and the reflux condenser temperature at the reactor head to $-30°$ C. by means of an external cryostat. A mixture formed of 0.5 liters/h (l/h) of elemental fluorine diluted with 0.5 liters/h of helium is fed for a total fluorine amount of 0.19 moles.

The reaction is followed by analyzing the gases outflowing from the reactor by IR and GC analyses which show $COF_2$ formation and the presence of fluorine.

When the reaction is over, the formed products, separated by filtration from the catalyst, are analyzed by $^{19}$F-NMR analysis. The conversion of initial —COF end groups to quantitatively give —$OCF_3$ groups is 54% with an yield of the fed fluorine of 81%.

The GC/MS and GC analyses, that throughout the examples of the present invention have been performed through the corresponding methyl esters, have shown the presence of the following reaction compounds a) (monoacylfluoride) and b) (neutral perfluoropolyether) together with the starting unreacted diacylfluorides c) in the following relative molar percentages, determined by gaschromatography:

| a) | $CF_3O\text{---}(CF_2CF_2O)_m(CF_2O)_n\text{---}CF_2C(O)F$ | 56% |
|---|---|---|
| b) | $CF_3O\text{---}(CF_2CF_2O)_m(CF_2O)_n\text{---}CF_3$ | 23% |
| c) | $F(O)CCF_2O\text{---}(CF_2CF_2O)_m(CF_2O)_n\text{---}CF_2C(O)F$ | 21% |

The yield of the monoacylfluorides a) calculated with respect to the initial converted diacylfluorides is 71%.

The reaction compounds are separated by fractional distillation.

Characterization of the products: $^{19}$F-NMR $^{19}$F-NMR spectrum in p.p.m. with respect to $CFCl_3$ (p.p.m.=0): 13.2 (1F $\underline{F}(O)CCF_2OCF_2O\text{---}$); 13.0 (1F $\underline{F}(O)CCF_2OCF_2CF_2O\text{---}$); $-51.7$, $-55.3$ (2F $\text{---}OC\underline{F}_2O\text{---}$); $-56.2$ (3F $C\underline{F}_3OCF_2CF_2O\text{---}$); $-57.8$ (3C$\underline{F}_3OCF_2O\text{---}$); $-87.5$ (3F $C\underline{F}_3CF_2O\text{---}$); $-88.4$, $-90.7$ (4F $\text{---}OCF_2C\underline{F}_2O\text{---}$).

The conditions used in this Example and the obtained results are summarized in Table 1.

Example 2

Syntesis in a semicontinuous way of monoacylfluoride $CF_3O\text{---}(CF_2CF_2O)_m(CF_2O)_n\text{---}CF_2C(O)F$ by performing the fluorination of the corresponding diacylfluorides over CsF catalyst at the temperature of 90° C.

In a 620 cc metal reactor equipped with reflux condenser, mechanical stirrer and internal thermocouple there are introduced 25 g of CsF catalyst which is activated as described in the Example 1.

After elimination of the residual fluorine, 500 g (0.806 moles) of diacylfluoride (IIIA) are introduced, then the reaction mixture is brought to 90° C. by a thermostatic oil bath and the reflux condenser temperature at the reactor top to −30° C. by means of an external cryostat. A mixture formed of 1.5 liters/h (l/h) of elemental fluorine diluted with 0.5 liters/h of helium is fed for a total fluorine amount of 1.11 moles.

The reaction is followed by analyzing the gases outflowing from the reactor by IR and GC analyses which show $COF_2$ formation and the presence of fluorine.

When the reaction is over, the formed products, separated by filtration from the catalyst, are analyzed by $^{19}F$-NMR analysis. The conversion of initial —COF end groups to quantitatively give —$OCF_3$ groups is 73% with an yield of the fed fluorine of 96%.

The GC/MS and GC analyses have shown the presence of the starting unreacted diacylfluorides c) and the formation of the following compounds: monoacylfluoride a) and neutral perfluoropolyether b), whose formulas have been reported in the Example 1.

The corresponding molar percentages, determined by gas-chromatography, are the following: a) 48%, b) 51%, c) 1%.

The yield of the monoacylfluorides a) calculated with respect to the initial converted diacylfluorides is 48%.

The reaction compounds are separated by fractional distillation.

Characterization of the products: $^{19}F$-NMR $^{19}F$-NMR spectrum in p.p.m. with respect to $CFCl_3$ (p.p.m.=0): 13.2 (1F $\underline{F}$(O)$CCF_2OCF_2O$—); 13.0 (1F $\underline{F}$(O) $CCF_2OCF_2CF_2O$—); −51.7, −55.3 (2F —$OC\underline{F}_2O$—); −56.2 (3F $C\underline{F}_3OCF_2CF_2O$—); −57.8 (3F $C\underline{F}_3OCF_2O$—); −87.5 (3F $C\underline{F}_3CF_2O$—); −88.4, −90.7 (4F —$OC\underline{F}_2C\underline{F}_2O$—).

The conditions used in this Example and the obtained results are summarized in Table 1.

By comparing the data of the Example 2 with those of the Example 1 it is noticed that in the Example 2 in the reaction products the starting diacylfluoride is substantially absent. This is particularly useful from an industrial point of view since it allows an easy separation of compound a) from the reaction mixture.

Example 3

Syntesis in a semicontinuous way of monoacylfluoride $CF_3O$—$(CF_2CF_2O)_m(CF_2O)_n$—$CF_2C(O)F$ by performing the fluorination of the corresponding diacylfluorides over CsF catalyst at the temperature of 65° C.

In a 620 cc metal reactor equipped with reflux condenser, mechanical stirrer and internal thermocouple there are introduced 5 g of CsF catalyst which is activated as described in the Example 1.

After elimination of the residual fluorine, 200 g (0.435 moles) of diacylfluoride are introduced, having formula:

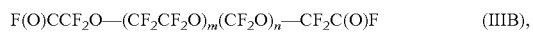

$$F(O)CCF_2O—(CF_2CF_2O)_m(CF_2O)_n—CF_2C(O)F \quad (IIIB),$$

average number MW (MN) 460, m/n ratio=4.50 and functionality in —COF end groups of 1.82 and functionality in —$CF_2CF_3$ end groups of 0.18, prepared as indicated in patents mentioned in the Example 1.

After the reaction mixture has been brought to 65° C. by a thermostatic oil bath and maintaining the reflux condenser temperature at −30° C. by means of an external cryostat, a mixture formed by 1.0 liters/h (l/h) of elemental fluorine diluted with 0.5 liters/h of helium is fed for a total fluorine amount of 0.54 moles.

The reaction is followed by analyzing the gases outflowing from the reactor by IR and GC analyses which show $COF_2$ formation and the presence of fluorine.

When the reaction is over, the formed compounds, separated by filtration from the catalyst, are analyzed by $^{19}F$-NMR analysis. The conversion of initial —COF end groups to quantitatively give —$OCF_3$ groups is 59% with an yield of the fed fluorine of 86%.

The GC/MS and GC analyses have shown the presence of the starting unreacted diacylfluorides c) and the formation of the following compounds: monoacylfluoride a) and neutral perfluoropolyether b), whose formulas have been reported in the Example 1.

The corresponding molar percentages, determined by gas-chromatography, are the following: a) 69%, b) 28%, c) 3%.

The yield of the monoacylfluorides a) calculated with respect to the initial converted diacylfluorides is 71%.

The reaction compounds are separated by fractional distillation.

Characterization of the products: $^{19}F$-NMR $^{19}F$-NMR spectrum in p.p.m. with respect to $CFCl_3$ (p.p.m.=0): 13.2 (1F $\underline{F}$(O)$CCF_2OCF_2O$—); 13.0 (1F $\underline{F}$(O) $CCF_2OCF_2CF_2O$—); −51.7, −55.3 (2F —$OC\underline{F}_2O$—); −56.2 (3F $C\underline{F}_3OCF_2CF_2O$—); −57.8 (3F $C\underline{F}_3OCF_2O$—); −87.5 (3F $C\underline{F}_3CF_2O$—); −88.4, −90.7 (4F —$OC\underline{F}_2C\underline{F}_2O$—).

The conditions used in this Example and the obtained results are summarized in Table 1.

Example 4

Syntesis in a semicontinuous way of monoacylfluoride $CF_3O$—$(CF_2CF_2O)_m(CF_2O)_n$—$CF_2C(O)F$ by performing the fluorination of the corresponding diacylfluorides over CsF catalyst at the temperature of 75° C.

In a 260 cc metal reactor equipped with reflux condenser, mechanical stirrer and internal thermocouple there are introduced 10 g of CsF catalyst (Aldrich®, titre 99.9%) which is activated as described in the Example 1.

After elimination of the residual fluorine, 100 g (0.161 moles) of diacylfluoride (IIIA) are introduced, then the reaction mixture is brought to 75° C. by a thermostatic oil bath and the reflux condenser temperature at the reactor top at −30° C. by means of an external cryostat. A mixture formed of 1.0 liters/h (l/h) of elemental fluorine diluted with 1.5 liters/h of helium is fed for a total fluorine amount of 0.13 moles.

The reaction is followed by analyzing the gases outflowing from the reactor by IR and GC analyses which show $COF_2$ formation and the presence of fluorine.

When the reaction is over, the formed products, separated by filtration from the catalyst, are analyzed by $^{19}F$-NMR analysis. The conversion of initial —COF end groups to quantitatively give —$OCF_3$ groups is 43% with an yield of the fed fluorine of 97%.

The GC/MS and GC analyses have shown the presence of the starting unreacted diacylfluorides c) and the formation of the following compounds: monoacylfluoride a) and neutral perfluoropolyether b), whose formulas have been reported in the Example 1.

The corresponding molar percentages, determined by gas-chromatography, are the following: a) 47%, b) 15%, c) 38%.

The yield of the monoacylfluorides a) calculated with respect to the initial converted diacylfluorides is 76%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F F(O)CCF$_2$OCF$_2$O—); 13.0 (1F F(O) CCF$_2$OCF$_2$CF$_2$O—); −51.7, −55.3 (2F —OCF$_2$O—); −56.2 (3F CF$_3$OCF$_2$CF$_2$O—); −57.8 (3F CF$_3$OCF$_2$O—); −87.5 (3F CF$_3$CF$_2$O—); −88.4, −90.7 (4F —OCF$_2$CF$_2$O—).

The conditions used in this Example and the obtained results are summarized in Table 1.

Example 5

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over CsF catalyst at the temperature of 90° C.

In a 420 cc metal reactor equipped with reflux condenser, mechanical stirrer and internal thermocouple there are introduced 12.5 g of CsF catalyst (Aldrich®, titre 99.9%) which is activated as described in the Example 1. Proceeding as described in the Example 1, 100 g (0.161 moles) of the diacylfluoride (IIIA) are introduced, then the reaction mixture is brought to 90° C. by a thermostatic oil bath and the reflux condenser temperature at the reactor top to −30° C. by means of an external cryostat. A mixture formed of 0.5 liters/h (l/h) of elemental fluorine diluted with 0.5 liters/h of helium is fed for a total fluorine amount of 0.082 moles.

The reaction is followed by analyzing the gases outflowing from the reactor by IR and GC analyses which show COF$_2$ formation and the presence of fluorine.

When the reaction is over, the formed compounds, separated by filtration from the catalyst, are analyzed by $^{19}$F-NMR analysis. The conversion of initial —COF end groups to quantitatively give —OCF$_3$ groups is 22% with an yield of the fed fluorine of 79%.

The GC/MS and GC analyses have shown the presence of the starting unreacted diacylfluorides c) and the formation of the following compounds: monoacylfluoride a) and neutral perfluoropolyether b), whose formulas have been reported in the Example 1.

The corresponding molar percentages, determined by gas-chromatography, are the following: a) 40%, b) 9%, c) 51%.

The yield of the monoacylfluorides a) calculated with respect to the initial converted diacylfluorides is 82%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F F(O) CCF$_2$OCF$_2$O—); 13.0 (1F F(O) CCF$_2$OCF$_2$CF$_2$O—); −51.7, −55.3 (2F —OCF$_2$O—); −56.2 (3F CF$_3$OCF$_2$CF$_2$O—); −57.8 (3F CF$_3$OCF$_2$O—); −87.5 (3F CF$_3$CF$_2$O—); −88.4, −90.7 (4F —OCF$_2$CF$_2$O—).

The conditions used in this Example and the obtained results are summarized in Table 1.

Example 6

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over KF catalyst at the temperature of 80° C.

In a 260 cc metal reactor equipped with reflux condenser, mechanical stirrer and internal thermocouple there are introduced 10 g of KF catalyst (Aldrich®, titre 99%) dried under gas stream inert at the temperature of 150° C. for two hours and subsequently fluorinated with 1 Nl/h of F$_2$ diluted with 1 Nl/h of He at the temperature of 150° C. for 2 hours.

After elimination of the residual fluorine, 100 g (0.161 moles) of diacylfluoride (IIIA) are introduced, then the reaction mixture is brought to 80° C. by a thermostatic oil bath maintaining the reflux condenser temperature at the reactor top at −30° C. by means of an external cryostat. A mixture formed of 1.0 liters/hour (l/h) of elemental fluorine diluted with 1.5 liters/h of helium is fed for a total fluorine amount of 0.17 moles.

The reaction is followed by analyzing the gases outflowing from the reactor by IR and GC analyses which show COF$_2$ formation and the presence of fluorine.

When the reaction is over, the formed compounds, separated by filtration from the catalyst, are analyzed by $^{19}$F-NMR analysis. The conversion of initial —COF end groups to quantitatively give —OCF$_3$ groups is 52%; the yield of the fed fluorine is 89%.

The GC/MS and GC analyses have shown the presence of the starting unreacted diacylfluorides c) and the formation of the following compounds: monoacylfluoride a) and neutral perfluoropolyether b), whose formulas have been reported in the Example 1.

The corresponding molar percentages, determined by gas-chromatography, are the following: a) 66%, b) 22%, c) 12%.

The yield of the monoacylfluorides a) calculated with respect to the initial converted diacylfluorides is 75%.

The reaction compounds are separated by fractional distillation. Characterization of the products: $^{19}$F-NMR $^{19}$F-NMR spectrum in p.p.m. with respect to CFCl$_3$ (p.p.m.=0): 13.2 (1F F(O) CCF$_2$OCF$_2$O—); 13.0 (1F F(O) CCF$_2$OCF$_2$CF$_2$O—); −51.7, −55.3 (2F —OCF$_2$O—); −56.2 (3F CF$_3$OCF$_2$CF$_2$O—); −57.8 (3F CF$_3$OCF$_2$O—); −87.5 (3F CF$_3$CF$_2$O—); −88.4, −90.7 (4F —OCF$_2$CF$_2$O—).

The conditions used in this Example and the obtained results are summarized in Table 1.

Example 7

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over CsF catalyst at the temperature of 100° C.

In a 620 cc metal reactor equipped with reflux condenser, mechanical stirrer and internal thermocouple and kept in an He inert atmosphere (He flow rate 2.0 liters/h) there are introduced 20 g of CsF catalyst (Acros®, titre 99.9%) and 700 g (1.13 moles) of the compound diacylfluoride (IIIA) as described in example 1.

The reaction mixture is brought to 100° C. by a thermostatic oil bath, maintaining the reflux condenser temperature at −40° C. by means of an external cryostat. A mixture formed by 1.5 liters/hour (l/h) of elemental fluorine diluted with 1.5 liters/h of He is fluxed, the total fluorine amount being of 1.87 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 75%; the fluorine calculated yield is 82%.

The GC/MS and GC analyses have shown the formation of the following compounds: monoacylfluoride a) and neutral perfluoropolyether b). No unreacted diacylfluorides c) have been detected. The formulas of the compounds a), b) and c) have been reported in Example 1.

The corresponding molar percentages, determined by gas-chromatography, are the following: a) 48%, b) 52%.

The yield of the monoacylfluoride a) calculated with respect to the converted diacylfluorides is 48%.

The reaction mixture has been hydrolized with 150 ml of 18% HCl aqueous solution and left under magnetic stirring at room temperature for 8 hours. The fluorinated organic phase has been separated and the monofunctional compound has been purified from the neutral perfluoropolyether compound b) by fractional distillation through vapour stream distillation.

The $^{19}$F-NMR, $^1$H-NMR and IR analyses performed on the distillate show that it is formed mainly by the neutral perfluoropolyethers compound b).

The residue of the distillation analyzed by $^{19}$F-NMR, $^1$H-NMR and IR, corresponds to a perfluoropolyether monocarboxylic compound of the following formula d)

$$CF_3O-(CF_2CF_2O)_m(CF_2O)_n-CF_2COOH \qquad d)$$

having a number average molecular weight of 620, m/n=4.7 and —COOH functionality of 1.0.

Characterization of the product $CF_3O-(CF_2CF_2O)_m(CF_2O)_n-CF_2COOH$:

$^{19}$F-NMR in p.p.m. with reference to CFCl$_3$ (p.p.m.=0): −51.7, −55.3 (2F —OC$\underline{F}_2$O—); −56.2 (3F C$\underline{F}_3$OCF$_2$CF$_2$O—); −57.8 (3F C$\underline{F}_3$OCF$_2$O—); −78.0 (2F —OCF$_2$CF$_2$OC$\underline{F}_2$COOH); −79.8 (2F -OCF$_2$OC$\underline{F}_2$COOH) −87.5 (3F C$\underline{F}_3$CF$_2$O—); −88.4, −90.7 (4F —OC$\underline{F}_2$C$\underline{F}_2$O—).

$^1$H-NMR in p.p.m. with reference to TMS (ppm=0): 7.9 (—COO$\underline{H}$).

IR: 1778 cm-1 (—COOH).

The conditions used in this Example and the obtained results are summarized in Table 2.

In this example the starting compounds c) is absent therefore it is easier the separation of pure compound a).

Example 8

Syntesis in a semicontinuous way of monoacylfluoride $CF_3O-(CF_2CF_2O)_m(CF_2O)_n-CF_2C(O)F$ by performing the fluorination of the corresponding diacylfluorides over CsF catalyst at the temperature of 120° C.

In a 620 cc metal reactor equipped with reflux condenser, mechanical stirrer and internal thermocouple and kept in an He inert atmosphere (He flow rate 2.0 liters/h) there are introduced 10 g of CsF catalyst (Acros®, titre 99.9%) and 700 g (1.13 moles) of the compound diacylfluoride (IIIA) as described in example 1.

The reaction mixture is brought to 120° C. by a thermostatic oil bath, maintaining the reflux condenser temperature at −40° C. by means of an external cryostat. A mixture formed by 1.5 liters/hour (l/h) of elemental fluorine diluted with 1.5 liters/h of He is fluxed, the total fluorine amount being of 1.34 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 54%; the fluorine calculated yield is 83%.

The GC/MS and GC analyses have shown the formation of the following compounds: monoacylfluoride a) and neutral perfluoropolyether b). Unreacted diacylfluorides c) have also been detected. The formulas of the compounds a), b) and c) have been reported in Example 1.

The corresponding molar percentages, determined by gas-chromatography, are the following: a) 62%, b) 25%, c) 13%.

The yield of the monoacylfluoride a) calculated with respect to the converted diacylfluorides is 71%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F $\underline{F}$(O)CCF$_2$O CF$_2$O—); 13.0 (1F $\underline{F}$(O)CCF$_2$OCF$_2$CF$_2$O—); −51.7, −55.3 (2F —OC$\underline{F}_2$O—); −56.2 (3F C$\underline{F}_3$OCF$_2$CF$_2$O—); −57.8 (3F C$\underline{F}_3$OCF$_2$O—); −87.5 (3F C$\underline{F}_3$CF$_2$O—); −88.4, −90.7 (4F —OC$\underline{F}_2$C$\underline{F}_2$O—).

The conditions used in this Example and the obtained results are summarized in Table 2.

Example 9

Syntesis in a semicontinuous way of monoacylfluoride $CF_3O-(CF_2CF_2O)_m(CF_2O)_n-CF_2C(O)F$ by performing the fluorination of the corresponding diacylfluorides over KF catalyst at the temperature of 100° C.

In a 620 cc metal reactor equipped with reflux condenser, mechanical stirrer and internal thermocouple and kept in an He inert atmosphere (He flow rate 2.0 liters/h) there are introduced 10 g of KF catalyst (Fluka purum>99%) and 700 g (1.13 moles) of the compound diacylfluoride (IIIA) as described in example 1.

The reaction mixture is brought to 100° C. by a thermostatic oil bath, maintaining the reflux condenser temperature at −40° C. by means of an external cryostat. A mixture formed by 1.5 liters/hour (l/h) of elemental fluorine diluted with 1.5 liters/h of He is fluxed, the total fluorine amount being of 1.27 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 55%; the fluorine calculated yield is 89%.

The GC/MS and GC analyses have shown the formation of the following compounds: monoacylfluoride a) and neutral perfluoropolyether b). Unreacted diacylfluorides c) have also been detected. The formulas of the compounds a), b) and c) have been reported in Example 1.

The corresponding molar percentages, determined by gas-chromatography, are the following: a) 66%, b) 25%, c) 9%.

The yield of the monoacylfluoride a) calculated with respect to the converted diacylfluorides is 72%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F $\underline{F}$(O)CCF$_2$O CF$_2$O—); 13.0 (1F $\underline{F}$(O)CCF$_2$OCF$_2$CF$_2$O—); −51.7, −55.3 (2F —OC$\underline{F}_2$O—); −56.2

(3F C$\underline{F}_3$OCF$_2$CF$_2$O—); −57.8 (3F C$\underline{F}_3$OCF$_2$O—); −87.5 (3F C$\underline{F}_3$CF$_2$O—); −88.4, −90.7 (4F —OC$\underline{F}_2$C$\underline{F}_2$O—).

The conditions used in this Example and the obtained results are summarized in Table 2.

Example 10

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over KF catalyst at the temperature of 120° C.

In a 620 cc metal reactor equipped with reflux condenser, mechanical stirrer and internal thermocouple and kept in an He inert atmosphere (He flow rate 2.0 liters/h) there are introduced 20 g of KF catalyst (Fluka purum >99%) and 700 g (1.13 moles) of the compound diacylfluoride (IIIA) as described in example 1.

The reaction mixture is brought to 120° C. by a thermostatic oil bath, maintaining the reflux condenser temperature at −40° C. by means of an external cryostat. A mixture formed by 2.0 liters/hour,(l/h) of elemental fluorine diluted with 2.0 liters/h of He is fluxed, the total fluorine amount being of 1.70 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 68%; the fluorine calculated yield is 82%.

The GC/MS and GC analyses have shown the formation of the following compounds: monoacylfluoride a) and neutral perfluoropolyether b). No unreacted diacylfluorides c) have been detected. The formulas of the compounds a), b) and c) have been reported in Example 1.

The corresponding molar percentages, determined by gas-chromatography, are the following: a) 63%, b) 37%.

The yield of the monoacylfluoride a) calculated with respect to the converted diacylfluorides is 63%.

The compounds a) and b) have been separated with the same procedure as described in ex. 7.

The residue of the distillation analyzed by $^{19}$F-NMR, $^1$H-NMR and IR, corresponds to a perfluoropolyether monocarboxylic compound of the following formula d):

CF$_3$O—(CF$_2$CF$_2$O)$_m$(CF$_2$O)$_n$—CF$_2$COOH          d)

having a number average molecular weight of 620, m/n=4.7 and —COOH functionality of 1.0.

Characterization of the product CF$_3$O—(CF$_2$CF$_2$O)$_m$(CF$_2$O)$_n$—CF$_2$COOH:

$^{19}$F-NMR in p.p.m. with reference to CFCl$_3$ (p.p.m.=0): −51.7, −55.3 (2F —OC$\underline{F}_2$O—); −56.2 (3F C$\underline{F}_3$OCF$_2$CF$_2$O—); −57.8 (3F C$\underline{F}_3$OCF$_2$O—); −78.0 (2F —OCF$_2$CF$_2$OC$\underline{F}_2$COOH); −79.8 (2F —OCF$_2$OC$\underline{F}_2$COOH) −87.5 (3F C$\underline{F}_3$CF$_2$O—); −88.4, −90.7 (4F —OC$\underline{F}_2$C$\underline{F}_2$O—).

$^1$H-NMR in p.p.m. with reference to TMS (ppm=0): 7.9 (—COOH).

IR:1778 cm-1 (—COOH).

The conditions used in this Example and the obtained results are summarized in Table 2.

Example 11

Syntesis in a semicontinuous way of monoacylfluoride CF$_3$O—(CF$_2$CF$_2$O)$_m$(CF$_2$O)$_n$—CF$_2$C(C)F by performing the fluorination of the corresponding diacylfluorides over NaF catalyst at the temperature of 100° C.

In a 260 cc metal reactor equipped with reflux condenser, mechanical stirrer and internal thermocouple and kept in an He inert atmosphere (He flow rate 2.0 liters/h) there are introduced 10 g of NaF catalyst (Aldrich Chemical Co. A.C.S. reagent 99+%) and 100 g (0.161 moles) of the compound diacylfluoride (IIIA) as described in example 1.

The reaction mixture is brought to 100° C. by a thermostatic oil bath, maintaining the reflux condenser temperature at −40° C. by means of an external cryostat. A mixture formed by 1.0 liters/hour (l/h) of elemental fluorine diluted with 1.5 liters/h of He is fluxed, the total fluorine amount being of 0.22 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 66%; the fluorine calculated yield is 88%.

The GC/MS and GC analyses have shown the formation of the following compounds: monoacylfluoride a) and neutral perfluoropolyether b). Unreacted diacylfluorides c) have also been detected. The formulas of the compounds a), b) and c) have been reported in Example 1.

The corresponding molar percentages, determined by gas-chromatography, are the following: a) 51%, b) 45%, c) 4%.

The yield of the monoacylfluoride a) calculated with respect to the converted diacylfluorides is 53%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F $\underline{F}$(O)CCF$_2$O CF$_2$O—); 13.0 (1F $\underline{F}$(O)CCF$_2$OCF$_2$CF$_2$O—); −51.7, −55.3 (2F —OC$\underline{F}_2$O—); −56.2 (3F C$\underline{F}_3$OCF$_2$CF$_2$O—); −57.8 (3F C$\underline{F}_3$OCF$_2$O—); −87.5 (3F C$\underline{F}_3$CF$_2$O—); −88.4, −90.7 (4F —OC$\underline{F}_2$C$\underline{F}_2$O—).

The conditions used in this Example and the obtained results are summarized in Table 2.

Example 12

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over CaF$_2$ catalyst at the temperature of 100° C.

Example 11 was repeated but using 10 g of CaF$_2$ catalyst (Merck 99%) instead of NaF.

When the reaction is over, the formed compounds, separated by filtration from the catalyst, are analyzed by $^{19}$F-NMR analysis. The conversion of the initial —COF end groups to quantitatively give —OCF$_3$ groups is 63%; the fluorine calculated yield is 84%.

The GC/MS and GC analyses have shown the formation of the following compounds: monoacylfluoride a) and neutral perfluoropolyether b). Unreacted diacylfluorides c) have also been detected. The formulas of the compounds a), b) and c) have been reported in Example 1.

The corresponding molar percentages, determined by gas-chromatography, are the following: a) 55%, b) 39%, c) 6%.

The yield of the monoacylfluoride a) calculated with respect to the converted diacylfluorides is 59%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F F(O)CCF$_2$OCF$_2$O—); 13.0 (1F F(O) CCF$_2$OCF$_2$CF$_2$O—); −51.7, −55.3 (2F —OCF$_2$O—); −56.2 (3F CF$_3$OCF$_2$CF$_2$O—); −57.8 (3F CF$_3$OCF$_2$O—); −87.5 (3F CF$_3$CF$_2$O—); −88.4, −90.7 (4F —OCF$_2$CF$_2$O—).

The conditions used in this Example and the obtained results are summarized in Table 2.

Example 13

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over KHF$_2$ catalyst at the temperature of 80° C.

In a 260 cc metal reactor equipped with reflux condenser, mechanical stirrer and internal thermocouple and kept in an He inert atmosphere (He flow rate 2.0 liters/h) there are introduced 20 g of KH.HF(KHF$_2$) catalyst (Aldrich Chemical Co. 99.9%) and 200 g (0.32 moles) of the compound diacylfluoride (IIIA) as described in example 1.

The reaction mixture is brought to 80° C. by a thermostatic oil bath, maintaining the reflux condenser temperature at −40° C. by means of an external cryostat. A mixture formed by 1.0 liters/hour (l/h) of elemental fluorine diluted with 1.5 liters/h of He is fluxed, the total fluorine amount being of 0.45 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 58%; the fluorine calculated yield is 75%.

The GC/MS and GC analyses have shown the formation of the following compounds: monoacylfluoride a) and neutral perfluoropolyether b). Unreacted diacylfluorides c) have also been detected. The formulas of the compounds a), b) and c) have been reported in Example 1.

The corresponding molar percentages, determined by gas-chromatography, are the following: a) 54%, b) 32%, c) 14%.

The yield of the monoacylfluoride a) calculated with respect to the converted diacylfluorides is 63%.

The reaction compounds are separated by fractional distillation.

Characterization of the products: $^{19}$F-NMR $^{19}$F-NMR spectrum in p.p.m. with respect to CFCl$_3$ (p.p.m.=0): 13.2 (1F F(O)CCF$_2$O CF$_2$O—); 13.0 (1F F(O) CCF$_2$OCF$_2$CF$_2$O—); −51.7, −55.3 (2F —OCF$_2$O—); −56.2 (3F CF$_3$OCF$_2$CF$_2$O—); −57.8 (3F CF$_3$OCF$_2$O—); −87.5 (3F CF$_3$CF$_2$O—); −88.4, −90.7 (4F —OCF$_2$CF$_2$O—).

The conditions used in this Example and the obtained results are summarized in Table 2.

Example 14

Syntesis in a semicontinuous way of monoacylfluoride CF$_3$O—(CF$_2$CF$_2$O)$_m$(CF$_2$O)$_n$—CF$_2$C(O)F by performing the fluorination of the corresponding diacylfluorides over KF catalyst at the temperature of 150° C.

In a 260 cc metal reactor equipped with reflux condenser, mechanical stirrer and internal thermocouple and kept in an He inert atmosphere (He flow rate 2.0 liters>h) there are introduced 10 g of KF catalyst (Fluka purum>99%) and 200 g (0.165 moles) of the following diacylfluoride compound (IIIC):

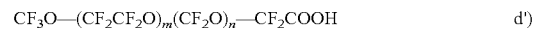

F(O)CCF$_2$O—(CF$_2$CF$_2$O)$_m$(CF$_2$O)$_n$—CF$_2$C(O)F    (IIIC), average number MW (MN) 1210, m/n ratio=2.11 and functionality in —COF end groups of 1.87 and functionality in —OCF$_3$ end groups of 0.13, determined by $^{19}$F-NMR. The diacylfluyoride (IIIC) has been prepared as described in U.S. Pat. No. 3,847,978.

The reaction mixture is brought to 150° C. by a thermostatic oil bath, maintaining the reflux condenser temperature at −40° C. by means of an external cryostat. A mixture formed by 1.0 liters/hour of elemental fluorine diluted with 1.5 liters/h of He is fluxed, the total fluorine amount being of 0.24 moles.

The reaction is followed by analyzing the gases outflowing from the reactor by IR and GC analyses, which show COF$_2$ formation and the presence of fluorine.

When the reaction is over, the formed compounds, separated by filtration from the catalyst, are analyzed by $^{19}$F-NMR analysis. The conversion of the initial —COF end groups to quantitatively give —OCF$_3$ groups is 72%; the fluorine calculated yield is 93%.

The reaction mixture has been hydrolized with 50 ml of 18% HCl aqueous solution and left under magnetic stirring at room temperature for 8 hours. The fluorinated organic phase has been separated and the monofunctional compound has been purified from the neutral perfluoro polyether compound b) by fractional distillation under vacumm (0.7 mm Hg) in the temperature range from 40° C. to 120° C. in order to separate mainly the neutral perfluoropolyethers compound b) (90 g).

The $^{19}$F-NMR, $^{1}$H-NMR, IR, GC/MS and GC analyses performed on the residue of the distillation (90 g) show that this is constituted of a perfluoropolyether mono-carboxylic compound of the following formula d')

CF$_3$O—(CF$_2$CF$_2$O)$_m$(CF$_2$O)$_n$—CF$_2$COOH    d')

with the following analytical features:
number average molecular weight (Mn) of 1420,
m/n=2.08,
—COOH functionality 0.96,
end groups CF$_3$O— functionality 1.04.

From the mass balance of the products recovered after distillation it is drawn that in the fluorination reaction are formed the monoacylfluoride compound a) and the neutral perfluoropolyether b). The above analytical data show that diacylfluorides c) are absent from the reaction mixture.

The yield of the isolated monoacylfluoride a) calculated with respect to the converted diacylfluorides is 38%.

Characterization of the product CF$_3$O—(CF$_2$CF$_2$O)$_m$ (CF$_2$O)$_n$—CF$_2$COOH:

$^{19}$F-NMR in p.p.m. with reference to CFCl$_3$ (p.p.m.=0): −51.7, −55.3 (2F —OCF$_2$O—); −56.2 (3FCF$_3$OCF$_2$ CF$_2$O—); −57.8 (3F CF$_3$OCF$_2$O—); −78.0 (2F —OCF$_2$CF$_2$ OCF$_2$COOH); −79.8 (2F —OCF$_2$OCF$_2$COOH) −87.5 (3F CF$_3$CF$_2$O—); −88.4, −90.7 (4F —OCF$_2$CF$_2$O—).

$^{1}$H-NMR in p.p.m. with reference to TMS (ppm=0): 12.5 (—COOH).

IR: 1778 cm-1 (—COOH).

The conditions used in this Example and the obtained results are summarized in Table 2.

TABLE 1

Examples 1-6. Summary of the features and obtained results.
In the Table, a), b) and c) are as defined in Ex. 1;
a) indicates monoacylfluoride, b) the neutral
perfluoropolyether, c) the starting
unreacted diacylfluoride.

| Ex. | way | M.W. (III) | Catal. | T (° C.) reaction | Conv. —COF —OCF$_3$/ —COF$_{init.}$ mol. % | yield a) % with respect to reacted diacylfl. (a + b) % mol. | F$_2$ conv. % mol. | % mol. int. final reaction mixture a) | b) | c) |
|---|---|---|---|---|---|---|---|---|---|---|
| 1 | semicont. | 620 | CsF | 90 | 54 | 71 | 81 | 56 | 23 | 21 |
| 2 | " | 620 | CsF | 90 | 73 | 48 | 96 | 48 | 51 | 1 |
| 3 | " | 460 | CsF | 65 | 59 | 71 | 86 | 69 | 28 | 3 |
| 4 | " | 620 | CsF | 75 | 43 | 76 | 97 | 47 | 15 | 38 |
| 5 | " | 620 | CsF | 90 | 22 | 82 | 79 | 40 | 9 | 51 |
| 6 | " | 620 | KF | 80 | 52 | 75 | 89 | 66 | 22 | 12 |

TABLE 2

Examples 7-14. Summary of the features and obtained results.
The headings of the columns in the Table are the same as in Table 1.

| Ex. | way | M.W. (III) | Catal. | T (° C.) reaction | Conv. —COF —OCF$_3$/ —COF$_{init.}$ mol. % | yield a) % with respect to reacted diacylfl. (a + b) mol. % | F$_2$ conv. % | % mol. int. final reaction mixture a) | b) | c) |
|---|---|---|---|---|---|---|---|---|---|---|
| 7 | semicont. | 620 | CsF | 100 | 75 | 48 | 82 | 48 | 52 | 0 |
| 8 | " | 620 | CsF | 120 | 54 | 71 | 83 | 62 | 25 | 13 |
| 9 | " | 620 | KF | 100 | 55 | 72 | 89 | 66 | 25 | 9 |
| 10 | " | 620 | KF | 120 | 68 | 63 | 82 | 63 | 37 | 0 |
| 11 | " | 620 | NaF | 100 | 66 | 53 | 88 | 51 | 45 | 4 |
| 12 | " | 620 | CaF$_2$ | 100 | 63 | 59 | 84 | 55 | 39 | 6 |
| 13 | " | 620 | KF.HF | 80 | 58 | 63 | 75 | 54 | 32 | 14 |

The invention claimed is:

1. A process for the synthesis of (per)fluorinated monofunctional carbonyl compounds having the following formula:

$$F\text{—}A\text{—}(R_F)_t\text{—}B\text{—}C(O)X_1 \quad (I)$$

wherein:

$X_1 = F, CF_3$;

$t = 0, 1$;

A, B equal to or different from each other, are independently $C_1$-$C_5$ (per)fluoroalkylene groups or linear or branched $C_1$-$C_5$ (per)fluorooxyalkylene groups, optionally containing one or more Cl and/or H atoms;

$R_F$ is selected from the following groups:

—Rf$_1$—, —ORf$_1$O— wherein Rf$_1$=$C_1$-$C_{20}$ perfluoroalkylene;

—ORf$_2$—, wherein Rf$_2$ is a perfluorooxyalkylene chain containing one or more of the following units statistically distributed along the backbone:

($C_3F_6O$), selected between ($CF_2CF(CF_3)O$) or ($CF(CF_3)CF_2O$);

($CFX_1O$) wherein $X_1$ is F or $CF_3$;

($C_2F_4O$);

($CF_2(CF_2)_{x'}CF_2O$) wherein x' is an integer equal to 1 or 2;

($CR_4R_5CF_2CF_2O$) wherein $R_4$, and $R_5$ are equal to or different from each other and selected between H, Cl, and wherein one fluorine atom of the perfluoromethylene unit is optionally substitued with H, Cl or (per)fluoroalkyl;

wherein the carbonyl groups of a (per)fluorinated di-functional carbonyl compound of formula:

$$X_2(O)C\text{—}A\text{—}(R_F)_t\text{—}B\text{—}C(O)X_1 \quad (III)$$

wherein:

$X_1$, $R_F$, t, A and B have the above meanings;

$X_2$, equal to or different from $X_1$, has the same meanings as $X_1$;

are fluorinated with elemental fluorine in the presence of a catalyst based on metal fluorides having formula MeFy.zHF, Me being an alkaline or alkaline-earth metal or Ag, y=1 or 2, z being an integer equal to 0, carrying out said reaction at a temperature in the range of 40° C. to 300° C. such that it leads to the formation of $C(O)FX_2$ wherein $X_2$ is as above, said fluorination being carried out by using a fluorine amount which at most is the necessary amount to obtain the total conversion of the starting compound (III).

2. A process according to claim 1, wherein, when t=0 and $X_1=X_2=F$, A or B is different from —$CF_2$—.

3. A process according to claim 1, wherein the A and B groups in the formulas (I)-(III) are selected from the following:

—CF$_2$—, —CF(CF$_3$)—, —CF$_2$CF$_2$—, —CF$_2$CF$_2$CF$_2$—, —CF$_2$CF(CF$_3$)—, —CF(CF$_3$)CF$_2$—, —CF(OCF$_3$)—, —C(OCF$_3$)$_2$—, —C(CF$_3$) (OCF$_3$)—.

4. A process according to claim 1, wherein when R$_F$=—ORf$_2$—, the perfluorooxyalkylene chain Rf$_2$ is selected from the following:

a') —(CF$_2$CF$_2$O)$_m$(CF$_2$O)$_n$(CF$_2$CF(CF$_3$)O)$_p$(CF(CF$_3$)O)$_q$ (CF$_2$CF$_2$CF$_2$O)$_r$, b') —(CF$_2$O)$_n$(CF$_2$CF(CF$_3$)O)$_p$(CF(CF$_3$)O)$_q$—, c') —(CF$_2$CF$_2$O)$_m$(CF$_2$O)$_n$—, wherein:
m is in the range from 0 to 100,
n is in the range from 0 to 100,
p is in the range from 0 to 60,
q is in the range from 0 to 60,
r is in the range from 0 to 60, m+n+p+q+r being ≧0 and the average molecular weight of —ORf$_2$— in the range 16-12,000.

5. A process according to claim 4, wherein in the formula c') when m and n are both present, m/n ranges from 0.2 to 12 and the number average molecular weight of —ORf$_2$ is within the values indicated in claim 4.

6. A process according to claims 1, wherein the reaction temperature ranges from preferably from 40° C. to 200° C.

7. A process according to claims 1, wherein the gaseous fluorine, optionally diluted with a gas inert under the reaction conditions, is fed at the above temperatures until obtaining a conversion percentage of the initial carbonyl end groups in the range 5%-90%.

8. A process according to claims 1, wherein the fluorine conversion is higher than 80%.

9. A process according to claims 1, carried out in a semi-continuous or continuous way.

10. A process according to claims 1, wherein the metal fluoride catalysts, are selected among the following:
alkaline or alkaline-earth metal fluorides selected from the following: CsF, KF, RbF, LiF, NaF, CaF$_2$, BaF$_2$, MgF$_2$, SrF$_2$;
AgF;
said catalysts being used as such, or mixed with each other or optionally supported on porous material.

11. A process according to claim 10, wherein the metal fluorides are CsF, KF, NaF, CaF$_2$.

12. A process according to claims 1, wherein the difunctional carbonyl (per) fluorinated compounds of formula (III) are selected from the following:

X$_2$(O)CCFY$_2$—O(CF$_2$O)$_n$(CF$_2$CF(CF$_3$)O)$_p$(CF(CF$_3$)O)$_q$—CFY$_1$C(O)X$_1$,

X$_2$(O)CCFY$_2$—O(CF$_2$CF$_2$O)$_m$, (CF$_2$O)$_n$—CFY$_1$C(O)X$_1$, wherein:
X$_1$, X$_2$, equal or different, are as above,
Y$_1$, Y$_2$, equal or different, have the X$_1$ meaning, m, n, p, q are as above.

13. A process according to claim 12, wherein the compounds of formula (III) are selected from the following:

F(O)CCF$_2$O(CF$_2$O)$_n$—CF$_2$C(O)F,

F(O)CCF$_2$O(CF$_2$CF$_2$O)$_m$—CF$_2$C(O)F,

F(O)CCF$_2$O(CF$_2$CF$_2$O)$_m$(CF$_2$O)$_n$—CF$_2$C(O)F, wherein m and n are as above defined.

14. A process according to claims 12, wherein the formula (III) compounds are selected from the following:

F(O)CCF$_2$OCF$_2$C(O)F, F(O)CCF$_2$OCF$_2$OCF$_2$C(O)F,

F(O)CCF$_2$OCF$_2$CF$_2$OCF$_2$C(O)F,

F(O)CCF$_2$OCF$_2$OCF$_2$CF$_2$OCF$_2$C(O)F, F(O)CCF$_2$OCF$_2$OCF$_2$OCF$_2$C(O)F,

F(O)CCF$_2$OCF$_2$CF$_2$OCF$_2$CF$_2$OCF$_2$C(O)F.

15. A process according to claim 7, wherein the conversion percentage of the initial carbonyl end groups is in the range 10%-80%.

16. A process according to claim 4, wherein the average molecular weight of —ORf$_2$— is in the range of 16-6,000.

17. A process according to claim 4, wherein the average molecular weight of —ORf$_2$— is in the range of 60-4,000.

18. A process according to claim 1, wherein the (per) fluoroalkyl has 1 to 4 carbon atoms.

* * * * *